US00PP37230P3

(12) United States Plant Patent
Bacon et al.

(10) Patent No.: US PP37,230 P3
(45) Date of Patent: Jan. 27, 2026

(54) GRAPEVINE PLANT NAMED 'SUGRA67'

(50) Latin Name: *Vitis vinifera*
Varietal Denomination: SUGRA67

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/041,826

(22) Filed: Jan. 30, 2025

(65) Prior Publication Data

US 2025/0301928 P1 Sep. 25, 2025

(30) Foreign Application Priority Data

Mar. 22, 2024 (PE) ..... 543-2024/DIN

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./207
See application file for complete search history.

*Primary Examiner* — Shubo Zhou
*Assistant Examiner* — Zachariah Allan Kay
(74) *Attorney, Agent, or Firm* — Knobbe, Martens, Olson & Bear, LLP

(57) ABSTRACT

The new variety of grapevine 'SUGRA67' is characterized by the production of a large-sized, black and obtuse ovoid berry with an early season ripening date. The berries of 'SUGRA67' are firm and somewhat juicy.

1 Drawing Sheet

Latin name of the genus and species claimed: *Vitis vinifera.*

Variety denomination: 'SUGRA67'.

CROSS-REFERENCE TO RELATED APPLICATIONS

This application claims the benefit of Peruvian Application No. 543-2024/DIN, filed on Mar. 22, 2024, which is incorporated by reference herein in its entirety.

BACKGROUND AND SUMMARY

This application relates to the discovery and asexual propagation of a new and distinct variety of grapevine, 'SUGRA67', as herein described and illustrated. The new variety was first selected as breeder number 'GR945B' by Terry A. Bacon and Terrence J. Frett in Wasco, Kern County, California in July 2020. The variety was originated by controlled hybridization.

The new variety 'SUGRA67' is characterized by the production of a large-sized, black and obtuse ovoid berry with an early season ripening date. The berries of 'SUGRA67' are firm and somewhat juicy.

The seed parent is 'Sugrasixteen' (U.S. Plant Pat. No. 11,749) and the pollen parent is 'GR439B' (Unpatented). The parent varieties were first crossed in April 2018. The date of first sowing is March 2019, and the date of first flowering is April 2020.

The new variety 'SUGRA67' was first asexually propagated in December 2020 in Wasco, Kern County, California, by Terry A. Bacon and Terrence J. Frett using hardwood cuttings.

The fruit of the new variety 'SUGRA67' has black obtuse ovate berries like its seed parent 'Sugrasixteen' (U.S. Plant Pat. No. 11,749), but the berry weight of the new variety 'SUGRA67' is 7 g, compared to 3.4 g for 'Sugrasixteen'. Additionally, the berries of the new variety 'SUGRA67' begin ripening about July 1 compared to July 20 for the berries of 'Sugrasixteen'.

The new variety 'SUGRA67' is similar to its pollen parent 'GR439B' (Unpatented) in that both varieties have black berries with rudimentary seed traces, but the new variety 'SUGRA67' has obtuse ovate shaped berries compared to round shaped berries for 'GR439B'. Additionally, 'SUGRA67' has a berry weight of 7 g compared to 6.2 g for 'GR439B'.

The fruit of the new variety 'SUGRA67' has black berries like 'Sugrafortyfive' (U.S. Plant Pat. No. 27,424), but the berry shape is obtuse ovate for the new variety 'SUGRA67' compared to narrow elliptic for 'Sugrafortyfive'. Additionally, 'SUGRA67' has a cluster weight of 700 g compared to 500 g for 'Sugrafortyfive'.

The fruit of the new variety 'SUGRA67' has rudimentary seed traces like the fruit of 'Summer Royal' (Unpatented), but the berry weight of the new variety 'SUGRA67' is 7 g compared to 5.7 g for 'Summer Royal'. Additionally, 'SGURA67' has a cluster weight of 700 g compared to 550 g for 'Sumer Royal'. Further, the berries of the new variety 'SUGRA67' begin ripening about July 1 compared to July 7 for the berries of 'Summer Royal'.

The new variety 'SUGRA67' has black berries like 'Sugrafortynine' (U.S. Plant Pat. No. 29,274), but the berry weight is 7 g for 'SUGRA67' compared to 5 g for 'Sugrafortynine'. Further, the berry shape of the new variety 'SUGRA67' is obtuse ovate compared to narrow elliptic for 'Sugrafortynine'.

The new variety 'SUGRA67' has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'SUGRA67'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2015.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA67' plants grown in the vicinity of Wasco, Kern County, California during 2022, and is believed to apply to plants of the variety grown under similar conditions of soil and climate elsewhere.

VINE

General: (Measurements taken on a three-year-old plant).

- *Vine size*.—Large. Height: Approximately 2.0 m. Width: Approximately 2.5 m.
- *Productivity*.—Very productive.
- *Crop load*.—Approximately 30 kg per vine after thinning.
- *Own root*.—Yes.
- *Training method*.—Typically cane pruned, leaving 6 canes.
- *Resistance*.—Neither resistance nor susceptibility to particular diseases or pests has been observed in this variety.

Trunk:

- *Shape*.—Stocky.
- *Diameter*.—Approximately 5.1 cm (at 30 cm above the soil line).
- *Straps*.—Short.
- *Inner and outer bark color*.—Inner bark about Medium Greyed-Orange 166C and weathering to about Dark Greyed-Green 197B in the outer bark.

SHOOTS

Young shoot:

- *Form of tip*.—Half open.
- *Density of prostrate hairs on tip*.—Absent or very sparse.
- *Density of erect hairs on tip*.—Absent or very sparse.
- *Color*.—About Medium Green 143C.

Woody shoot (observations made in the middle third of shoot):

- *Attitude before tying*.—Semi-drooping.
- *Growth of axillary shoots*.—Medium, about 17 to 21 cm in length.
- *Internode length*.—Very short, approximately 50 mm.
- *Width at node*.—Approximately 10 mm.
- *Cross section*.—Circular.
- *Surface texture*.—Striate.
- *Main color*.—About Medium Greyed-Orange 166C.
- *Color of dorsal side of internode*.—About Medium Greyed-Orange 166C.
- *Color of ventral side of internode*.—About Medium Greyed-Orange 166C.
- *Color of dorsal side of node*.—About Dark Greyed-Orange 166A and Medium Greyed-Orange 166C.
- *Color of ventral side of node*.—About Dark Greyed-Orange 166A and Medium Greyed-Orange 166C.
- *Density of erect hairs on nodes:* Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 2 mm.
- *Color*.—About Light Green 141D in mid-summer.
- *Form*.—Bifurcated.
- *Number of consecutive tendrils*.—Up to 2.
- *Length of tendril*.—Medium, approximately 15 cm.

LEAVES

Young leaves:

- *Color of upper surface of first* 4 *distal unfolded leaves*.—About Medium Green 143C.
- *Average intensity of anthocyanin coloration of six distal leaves prior to flowering*.—Present, covers about 50% of surface of the six distal leaves prior to flowering.
- *Density of prostrate hairs between veins at lower surface of* 4*th distal unfolded leaf*.—Absent or very sparse.
- *Density of erect hairs between veins at lower surface of* 4*th distal unfolded leaf*.—Absent or very sparse.
- *Density of prostrate hairs on veins at lower surface of* 4*th distal unfolded leaf*.—Absent or very sparse.
- *Density of erect hairs on veins at lower surface of* 4*th distal unfolded leaf*.—Absent or very sparse.

Mature leaves (observations made on leaves in the middle third of the shoot):

- *Size*.—Large.
- *Average length*.—Approximately 12 cm.
- *Average width*.—Approximately 14 cm.
- *Shape of blade*.—Pentagonal.
- *Number of lobes*.—Approximately 5.
- *Mature leaf profile*.—Undulate.

*Blistering surface of blade upper surface*.—Absent or very weak.
*Leaf blade tip*.—In the plane of the leaf.
*Undulation of margin*.—Slightly undulating.
*Thickness*.—Average-typical of *Vitis vinifera* species.
*Overall shape of teeth*.—Mixture of both sides straight and both sides convex.
*Length of teeth*.—Medium, ranging from about 5 mm to 10 mm.
*Ratio length/width of teeth*.—Very small, nearly 1:1.
*General shape of petiole sinus lobes*.—Wide open.
*Tooth at petiole sinus*.—Absent.
*Petiole sinus limited by veins*.—Absent.
*Shape of upper lateral sinus lobes*.—Closed.
*Depth of upper lateral sinuses*.—Medium, approximately 2 cm to 4 cm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Usually about Light Green 138B becoming about Medium Grey-Brown 199C.

Upper leaf surface:
*Color*.—About Medium Green 139B.
*Surface texture*.—Smooth.
*Surface appearance*.—Dull.
*Anthocyanin coloration of main veins*.—Absent or very low.

Lower leaf surface:
*Color*.—About Medium Green 143A.
*Surface texture*.—Smooth.
*Surface appearance*.—Dull.
*Anthocyanin coloration of main veins*.—Low.

Petiole:
*Length of petiole*.—Approximately 6 cm.
*Diameter*.—Approximately 3 mm.
*Length of petiole compared to middle vein*.—Much shorter, 6 cm for the petiole compared to 12 cm for middle vein.
*Density of prostrate hairs on petiole*.—Absent.
*Density of erect hairs on petiole*.—Absent.
*Color*.—About Medium Greyed-Orange 172A and Medium Greyed-Orange 173A.

Buds:
*Shape*.—Conical.
*Size*.—Medium, approximately 3 mm wide×4 mm long.
*Position*.—Slightly held out.
*Bud fruitfulness*.—Basal, mostly fruitful.
*Time of bud burst*.—Early, approximately March 15th for the southern San Joaquin Valley region of California.

FLOWERS

General:
*Flower type*.—Fully developed stamen and fully developed gynoecium.
*Position of first flowering node*.—Usually 3rd node of current season growth.
*Number of inflorescences per shoot*.—Usually 1.2 per shoot.
*Time of full bloom*.—Approximately May 9th in the southern San Joaquin Valley region of California.

FRUIT

General:
*Ripening period*.—Early season, beginning about July 1st in the southern San Joaquin Valley region of California.
*Use*.—Fresh market.
*Storage quality*.—Commercially acceptable fruit after 6 weeks of storage at storage temperatures ranging from 30° F. to 32° F. and 90% to 95% humidity.

Cluster:
*Form*.—Winged, double cluster.
*Cluster size* (*peduncle excluded*).—Large.
*Cluster length* (*peduncle excluded*).—Approximately 17 cm.
*Cluster width*.—Approximately 15 cm.
*Cluster weight*.—Approximately 700 g.
*Cluster density*.—Medium, loose-full.
*Number of berries*.—Approximately 90 berries after tipping.

Peduncle:
*Length*.—Long, approximately 3 cm.
*Diameter*.—Approximately 7 mm.
*Lignification of peduncle*.—Weak.
*Color*.—About Medium Green 141C.

Berry:
*Size*.—Large, approximately 7 g.
*Dimensions*.—Width: Approximately 21 mm. Length: Approximately 30 mm.
*Uniformity of size*.—Somewhat uniform.
*Shape*.—Obtuse ovoid.
*Cross section*.—Circular.
*Skin color* (*without bloom*).—About Black 203C.
*Flesh color*.—About Medium Green 139C and Medium Greyed-Purple 185C.
*Bloom* (*cuticular wax*).—Medium, typical of most commercial *Vitis vinifera*.
*Pedicel length*.—Approximately 8 mm.
*Pedicel thickness*.—Thin, approximately 1.6 mm.
*Seed traces*.—Rudimentary.
*Flesh texture*.—Firm.
*Particular flavor*.—None.
*Refractometer test*.—About 19 Brix.
*Juice pH*.—About 3.31.
*Titratable acidity*.—About 0.47%.
*Brix*.—Acid Ratio: Approximately 40.4.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA67' as herein illustrated and described.

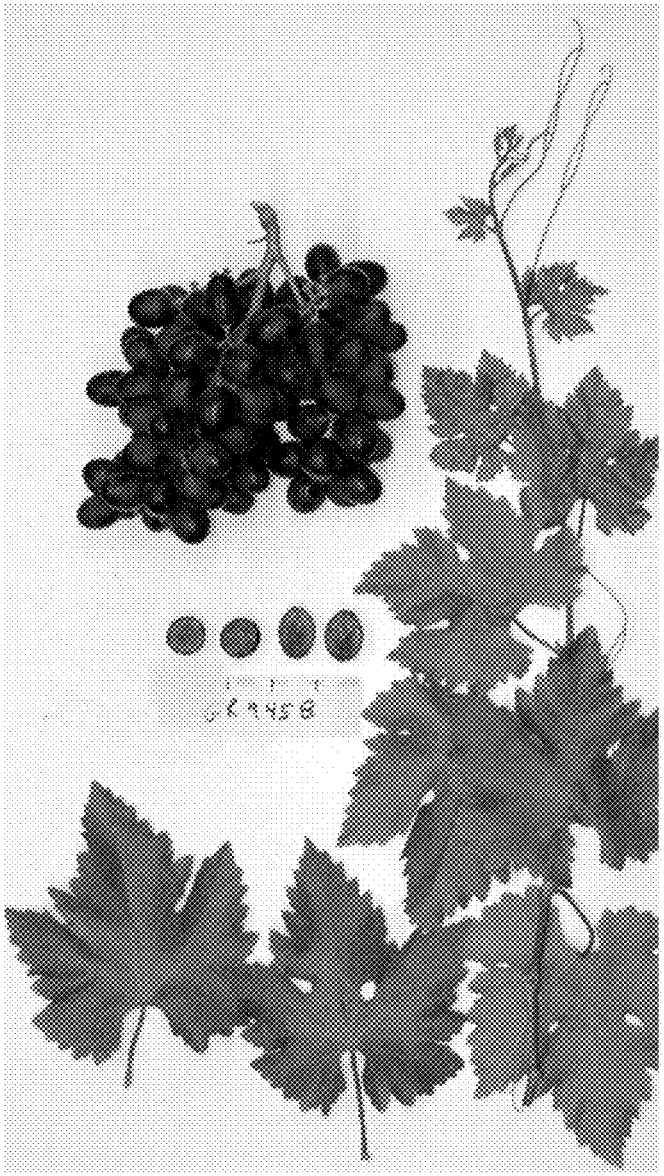

* * * * *